United States Patent [19]

Ramert et al.

[11] Patent Number: 5,264,573

[45] Date of Patent: Nov. 23, 1993

[54] PROCESS FOR PREPARING 2-CHLORO-1,7-DIHYDROPURIN-6-ONE AND A PROCESS FOR ITS PURIFICATION

[75] Inventors: Reiner Ramert, Weiler Bei Bingen; Albrecht Christmann, Ingelheim am Rhein, both of Fed. Rep. of Germany

[73] Assignee: Boehringer Ingelheim GmbH, Ingelheim am Rhein, Fed. Rep. of Germany

[21] Appl. No.: 729,517

[22] Filed: Jul. 12, 1991

[30] Foreign Application Priority Data

Jul. 13, 1990 [DE] Fed. Rep. of Germany ....... 4022314

[51] Int. Cl.$^5$ ................... C07D 473/40; C07B 37/00
[52] U.S. Cl. ............................................... 544/265
[58] Field of Search .......................... 544/265, 264

[56] References Cited

U.S. PATENT DOCUMENTS 2,815,346 12/1957 Hitchings et al. ................. 544/264
4,405,781 9/1983 Bader et al. ........................ 544/264

FOREIGN PATENT DOCUMENTS 001952 2/1966 Japan ................................. 544/264

OTHER PUBLICATIONS

Neiman Isr. J. Chem 3, 161 (1965).
Hurst, "Introduction to the Chemistry and Biochemistry of Pyrandines" pp. 64–81 (1980).

*Primary Examiner*—Mark L. Berch
*Attorney, Agent, or Firm*—David E. Frankhouser; Alan R. Stempel; Mary-Ellen M. Timbers

[57] ABSTRACT

A process for the preparation of 2-chloro-1,7-dihydropurin-6-one which comprises the steps of:
a) suspending 2-thioxanthine in concentrated hydrocloric acid, to produce a suspension; and
b) contacting the suspension with chlorine, to produce 2-chloro-1,7-dihydropurin-6-one.

11 Claims, No Drawings

PROCESS FOR PREPARING 2-CHLORO-1,7-DIHYDROPURIN-6-ONE AND A PROCESS FOR ITS PURIFICATION

The invention relates to a process for the preparation and purification of 2-chloro-1,7-dihydropurin-6-one (2-chloro-hypoxanthine).

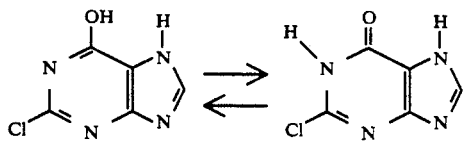

2-chlorohypoxanthine (I) is derived from the base-structure 9H-purine (which, when unsubstituted in the 7 and 9-positions, is in equilibrium with its tautomer 7H-purine [H. Beyer and W. Walter, Lehrbuch der organischen Chemie, S. Hirzel Verlag, Stuttgart 1988, p. 797]).

In past years, derivatives of the purines have undergone a stormy period of development in terms of their use as therapeutic agents [T. W. Stone Ed., Purines - Pharmacology and Physiological Roles, VCH Verlagsgesellschaft, Weinheim 1985].

Thus, a large number of nucleosides having a purine partial structure have antimetabolic properties. Some nucleoside derivatives have been found which are capable of restricting the replication of the HIV virus responsible for AIDS.

This group of effective nucleosides includes, in particular, nucleosides in which the so-called nucleoside base has a naturally occurring or derivatised purine system. The use of purine derivatives which are derivatised at the nitrogen atom in the 9-position and functionalised in the 2-position appear particularly promising [see also European Patent Application 343 133 and 291 917]. 2-Chlorohypoxanthine (I) would appear to be a suitable starting material for derivatised purines of this kind, being already suitably functionalised in the 2-position.

The processes hitherto known from the literature for preparing this attractive intermediate compound do, however, suffer from the defect that industrial production is only possible at high cost, or that the necessary educts are not commercially available.

Thus, J. A. Montgomery and L. B. Holum [J. Am. Chem. Soc. 79 (1957) 2185] describe a method of synthesis starting from 2,6-dichloropurine. A similar process is described by Y. Yamada et al. [Chemical Abstracts 66 (1967) 9536 8a]. The disadvantages of both methods are, in particular, the fact that the partial hydrolysis of the dichloro compound requires considerable dilution of the starting material and the 2-chlorohypoxanthine can only be isolated in a yield of 66% (crude product). Furthermore, 2,6-dichloropurine is expensive, not commercial available in large quantities and represents—because of its critical irritant, its allergenic and potential cancerogenic, character—a substance, the handling of which raises important problems with regard to safety engineering and working hygiene. These disadvantageous aspects indicate that this type of synthesis would be impractical for the industrial production of 2-chlorohypoxanthine.

The second method described in the literature starts from 2,8-dichloro-6-hydroxypurine [E. Fischer, Chem. Ber. 30 (1897) 2208; ibid. 30 (1897) 2226] which is not, however, commercially available and accordingly has first to be produced from uric acid and phosphorusoxychloride.

The 2,8-dichloro-6-hydroxypurine synthesised in this way has to be partially dehalogenated in another reaction step either with hydrogen iodide or by selective catalytic hydrogenolysis [H. Ballweg, Liebigs Ann. Chem. 649 (1961) 114]. Whereas dehalogenation with hydrogen iodide is very complex and impractical for industrial application, in catalytic hydrogenolysis the reaction product has to be recrystallised several times from water and is then obtained in a yield of only 77%, which means that this process is also unsuitable for adoption on an industrial scale.

In addition, very high standards have to be imposed on the purity criteria of intermediate products used in manufacturing methods for synthesising pharmaceuticals.

The aim of the present invention is to provide a process for preparing 2-chlorohypoxanthine (I) (2-chloro-1, 7-dihydropurin-6-one) which allows this purine derivative to be produced easily and in good yields.

A further objective of the present invention is to provide a method of synthesis in which the reaction products or intermediate products are obtained in a crystalline form which permits trouble-free further processing—centrifugation, drying, etc.—even of industrial-scale batches.

A further aim of the present invention is to provide a method of purification in which the 2-chlorohypoxanthine (I) is obtained in a degree of purity which allows the product to be used directly as a starting material in other processes for preparing pharmaceutically active substances.

In its broadest aspect, the invention provides a process for preparing 2-chlorohypoxanthine, which may be obtained in the form of a salt or a hydrate, the process comprising reacting 2-thioxanthine suspended in a concentrated hydrochloride acid, with chlorine.

Preparation of the
2-chlorohypoxanthine-hydrochloride monohydrate

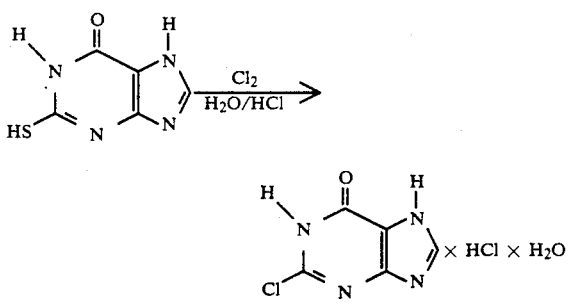

According to the invention, the objectives outlined above are achieved by first preparing the monohydrate of 2-chlorohypoxanthine-hydrochloride starting from commercial 2-thioxanthine by chlorination in the presence of concentrated hydrochloric acid. To do this, the 2-thioxanthine is first suspended in concentrated hydrochloric acid and chlorine is introduced into the reaction mixture over a period of 3 to 7 hours—preferably about 5 hours—at a temperature of 0° C. to 10° C.—preferably 2° C. to 7° C. and especially 3° C. to 5° C. Then some of the hydrochloric acid is distilled off and the reaction mixture is cooled to a temperature in the range from −5° C. to +10° C.—preferably 0° C. to 5° C.—to cause precipitation of the required 2-chlorohypoxanthine in the form of the monohydrate of its hydrochloric salt. The reaction mixture is then suction filtered and the crystalline residue is washed first with saline solution and then with an organic solvent, preferably an alcohol, especially isopropanol, and dried.

Preparation of the 2-chlorohypoxanthine

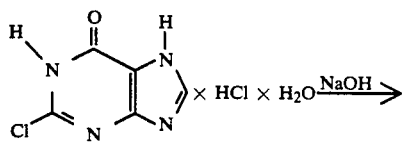

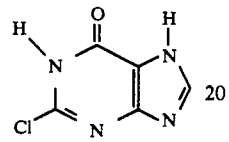

In a subsequent reaction step the 2-chlorohypoxanthine hydrochloride monohydrate is suspended in an aqueous solution at a pH ranging from 6 to 7 and, preferably, a pH of 6.5, which is adjusted with an aqueous solution of an alkali or alkaline earth metal hydroxide, preferably an alkali metal hydroxide and especially concentrated sodium hydroxide solution. After the suspension is heated to a temperature in the range from 50° C. to 70° C.—preferably 55° C. to 65° C. and more especially to a temperature of 60° C. The resulting solution is, if necessary, treated with decolorising charcoal and filtered. An aqueous solution of an acid is admixed with the solution to adjust the pH to a value in the range from 2 to 4 and, preferably, 3.0. The acid is preferably an inorganic acid and especially hydrochloric acid.

The resulting solution is cooled to a temperature in the range from −5° C. to +15° C.—preferably 5° C. to 10° C. to precipitate 2-chloro-hypoxanthine. The precipitate is washed with water and then with an organic solvent, preferably an alcohol, more particularly isopropanol, and dried.

Preparation of sodium 2-chlorohypoxanthine hydrate

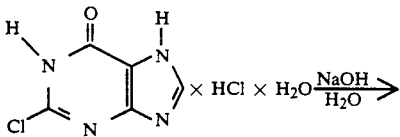

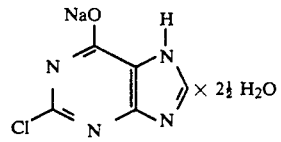

In order to prepare the sodium salt of 2-chlorohypoxanthine in highly pure form, 2-chloro-hypoxanthine-hydrochloride-monohydrate is suspended in water. Whilst cooling, the pH is adjusted to a value in the range from 9 to 10, preferably, 9.5 to 10, and more preferably, 9.7, using an aqueous solution of an inorganic base, preferably a solution of an alkali metal hydroxide and more preferably using concentrated sodium hydroxide solution.

The reaction mixture is then cooled to a temperature below ambient temperature, preferably to a temperature in the range from −2° C. to +10° C., more preferably 2° C. to 5° C. to precipitate the hydrate of the desired sodium salt. The crystalline precipitate is suction filtered and washed first with cooled brine and then with an organic solvent, preferably an alcohol and more especially isopropanol, and dried.

Preparation of high purity 2-chlorohypoxanthine (I)

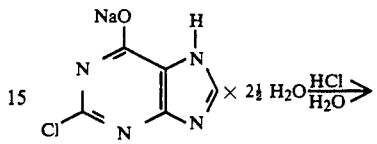

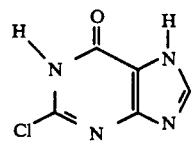

The pH of a suspension of sodium 2-chloro-hypoxanthine hydrate in water is adjusted to a value in the range of 6.5, using acid, preferably an inorganic acid and more especially dilute hydrochloric acid. The suspension is then heated to a temperature in the range from 55° C. to 65° C., preferably 60° C.

The resulting solution is filtered, optionally after treatment with decolorising charcoal. The pH of the filtrate is adjusted to a value in the range from 2 to 4, preferably a pH of 3.0, using an aqueous solution of an acid, preferably an inorganic acid and more particularly 1 N hydrochloric acid. The resulting suspension is then cooled to a temperature below ambient temperature, preferably to a temperature in the range from −2° C. to +15° C., more especially from 5 to 10° C., to precipitate the desired 2-chloro-hypoxanthine. The resulting precipitate is suction filtered and washed with water and then with an organic solvent, preferably an alcohol and more especially isopropanol.

The crystalline residue is dried. The 2-chloro-hypoxanthine obtained in this way has a purity of more than 99%, according to HPLC analysis.

The process steps explained above are described more accurately by the reaction sequence mentioned in the Examples. Various alternative embodiments of the process and the like will become apparent to anyone skilled in the art from the description. However, it is expressly pointed out that the Examples and the related specification are provided solely for the purpose of explanation and description and should not be regarded as a restriction of the invention.

EXAMPLES

1) Preparation of 2-chlorohypoxanthine-hydrochloride-monohydrate 230 g (3.24 mol) of chlorine are introduced into a suspension of 168.2 g (1.0 mol) of 2-thioxanthine in 68 liters of conc. hydrochloric acid in the course of about 5 hours at 3°–5° C. Then about 1 liter of hydrochloric acid is distilled off in a water jet vacuum, the residue is cooled to 0° to +5° C., suction filtered and washed with 0.5 liters of saturated, ice-cold brine and finally with 300 ml of isopropanol. After drying at 50° C. over a period of about 12 hours, 93 g (85.7% of theory) of colourless crystal powder are obtained. By preparing the free base and again converting it into the hydrochloride the title compound is obtained in analytically pure form. Elemental analysis corresponds to the composition $C_5H_4Cl_2N_4O \times H_2O$.

2) Preparation of 2-chlorohypoxanthine 180 g (0.80 mol) of 2-chlorohypoxanthine-hydrochloride-monohydrate are suspended in 3.6 liters of water and the pH is adjusted to 6.5 by the dropwise addition of concentrated sodium hydroxide solution. After heating to 60° C. the solution is treated with 18 g of decolorising charcoal and filtered. The filtrate is added dropwise to 300 ml of water, whilst a pH of 3.0 +/− 0.5 is maintained in the aqueous solution using 1N hydrochloric acid. The resulting suspension is cooled to 5°-10° C., suction filtered and the precipitate is washed with 0.5 liters of water at a temperature of +5° C. and with 300 ml of isopropanol. After drying at 50° C., 117 g (85.8% of theory) of the title compound are obtained in the form of a colourless crystal powder. By purifying via the sodium salt and re-liberation of the base, analytically pure material is obtained which is identical to the substance prepared from 2,6-dichloropurine according to J. A. Montgomery and L. B. Holum [J. Am. Chem. Soc. 79 (957) 2185].

3) Preparation of sodium 2-chlorohypoxanthine hydrate 80 g (0.3mol) of 2-chlorohypoxanthine-hydrochloride-monohydrate are suspended in 1.6 liters of water. Whilst cooling, a pH of 9.7 is adjusted using concentrated sodium hydroxide solution. After cooling to +5° C. the precipitate is suction filtered, then washed with 250 ml of 20% brine (previously cooled to +5° C.) and 250 ml of isopropanol. After drying at 50° C., 65.7 g (77.6% of theory) of the title compound are obtained in the form of a colourless crystal powder. By suspending in cold water and again suction filtering, washing with cold water and methanol and drying, an analytically pure product is obtained, the composition of which corresponds to the formula $C_5H_2ClN_4ONa \times 2.5H_2O$, according to elemental analysis.

4) Preparation of highly pure 2-chlorohypoxanthine 20 g of sodium 2-chlorohypoxanthine-hydrate are suspended in 400 ml of water, the pH is adjusted to 6.5 in the reaction solution using dilute hydrochloric acid and the mixture is heated to about 60° C. After treatment with 2 g of decolorising charcoal and filtration, the 2-chlorohypoxanthine is precipitated and isolated in the same way as described in Example 2 (at pH 3.0 +/− 0.5 and at ambient temperature). 11.6 g (8% of theory) of the title compound are obtained in the form of colourless crystals. According to HPLC analysis the product has a degree of purity of more than 99%.

What is claimed is:

1. A process for preparing 2-chlorohypoxanthine which comprises:
   a) suspending 2-thioxanthine in concentrated hydrochloric acid, to produce a first suspension; and
   b) contacting the first suspension with chlorine, to produce 2-chlorohypoxanthine.

2. A process as recited in claim 1 wherein the first suspension is contacted with the chlorine for about 3 to 7 hours.

3. A process as recited in claim 2 wherein the 2-chlorohypoxanthine produced is produced as a precipitate in the form of 2-chlorohypoxanthine hydrochloride monohydrate.

4. A process as recited in claim 3 which further comprises the steps of:
   c) suspending the 2-chlorohypoxanthine hydrochloride monohydrate in an aqueous solution of an alkali or alkaline earth metal hydroxide at a pH of from about 6 to 7, to produce a second suspension;
   d) heating the second suspension at a temperature of from about 50° C. to 70° C.;
   e) adjusting the pH of the suspension produced in b) to about 2 to 4; and
   f) cooling the suspension produced in c) to about −5° C. to 15° C., to produce 2-chlorohypoxanthine as a precipitate.

5. A process as recited in claim 3 which further comprises the steps of:
   c) suspending the 2-chlorohypoxanthine hydrochloride monohydrate in an aqueous solution of an alkali or alkaline earth metal hydroxide at a pH of about 9 to 10, to produce a third suspension; and
   d) cooling the third suspension to about −2° C. to 10° C., to produce a 2-chlorohypoxanthine hydrate as a precipitate.

6. A process for preparing 2-chlorohypoxanthine which comprises:
   a) suspending 2-thioxanthine in concentrated hydrochloric acid, to produce a first suspension;
   b) contacting the first suspension with chlorine, to produce a first reaction mixture;
   c) concentrating the first reaction mixture by evaporation, to produce a residue;
   d) cooling the residue to about −5° C. to 10° C., to produce 2-chlorohypoxanthine hydrochloride monohydrate as a precipitate;
   e) suspending the 2-chlorohypoxanthine hydrochloride monohydrate in an aqueous solution of an alkali or alkaline earth metal hydroxide at a pH of from about 6 to 7, to produce a second suspension;
   f) heating the second suspension to a temperature of about 50° C. to 70° C.;
   g) filtering the resultant suspension to produce an aqueous filtrate;
   h) adjusting the pH of the aqueous filtrate to about 2 to 4;
   i) cooling the adjusted aqueous filtrate produced in h) to about −5° C. to 10° C., to produce 2-chlorohypoxanthine as a precipitate.

7. A process as recited in claim 6 wherein:
   i) the 2-chlorohypoxanthine hydrochloride monohydrate is suspended in step e) in an aqueous solution of an alkali metal hydroxide at a pH of from about 6 to 7; and
   ii) the second suspension is heated to a temperature of about 55° C. to 65° C.

8. A process as recited in claim 6 wherein:
   i) the 2-chlorohypoxanthine hydrochloride monohydrate is suspended in step e) in an aqueous solution of sodium hydroxide at a pH of about 6.5;
   ii) the second suspension is heated to a temperature of about 60° C.;
   iii) the pH of the aqueous filtrate in step h) is adjusted to about 3; and
   iv) the adjusted aqueous filtrate in step i) is cooled to about 5° C. to 10° C.

9. A process for preparing 2-chlorohypoxanthine which comprises:

a) suspending 2-thioxanthine in concentrated hydrochloric acid, to produce a first suspension;
b) contacting the first suspension with chlorine, to produce a first reaction mixture;
c) concentrating the first reaction mixture by evaporation, to produce a residue;
d) cooling the residue to about −5° C. to 10° C., to produce 2-chlorohypoxanthine hydrochloride monohydrate as a precipitate;
e) suspending the 2-chlorohypoxanthine hydrochloride monohydrate in a aqueous solution of an inorganic base at a pH of about 9 to 10, to produce a second suspension;
f) cooling the second suspension to about −2° C. to 10° C., to produce a 2-chlorohypoxanthine hydrate as a precipitate;
g) suspending the 2-chlorohypoxanthine hydrate in water, to produce a third suspension;
h) adjusting the pH of the third suspension to about 6 to 7;
i) heating the adjusted third suspension produced in h) to a temperature of about 55° C. to 65° C.;
j) filtering the resultant suspension to produce an aqueous filtrate;
k) adjusting the pH of the aqueous filtrate to about 2 to 4;
l) cooling the adjusted aqueous filtrate produced in k) to about −2° C. to 15° C., to produce 2-chlorohypoxanthine as a precipitate.

10. A process as recited in claim 9 wherein the 2-chlorohypoxanthine hydrochloride monohydrate is suspended in an aqueous solution of an alkali metal hydroxide at a pH of about 9.5 to 10, to produce the second suspension.

11. A process as recited in claim 9 wherein:
i) the 2-chlorohypoxanthine hydrochloride monohydrate is suspended in an aqueous solution of sodium hydroxide at a pH of about 9.7 to produce the second suspension;
ii) the second suspension is cooled to about 2° C. to 5° C.;
iii) the third suspension is adjusted to pH 9.7 with sodium hydroxide;
iv) the adjusted third suspension of step j) is heated to about 60° C.;
v) the aqueous filtrate is adjusted to pH 3; and
vi) the adjusted aqueous filtrate is cooled to about 5° C. to 10° C.

* * * * *